United States Patent
Khosla et al.

(10) Patent No.: US 10,433,983 B1
(45) Date of Patent: Oct. 8, 2019

(54) ADJUSTABLE PIN SETTING TARGETER DEVICE

(71) Applicant: Arthrex, Inc., Naples, FL (US)

(72) Inventors: Rudraksh Khosla, Naples, FL (US); Nick Metcalfe, Bonita Springs, FL (US); Tyler Clevett, Bonita Springs, FL (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 16/382,140

(22) Filed: Apr. 11, 2019

(51) Int. Cl.
| | |
|---|---|
| *A61F 2/46* | (2006.01) |
| *A61B 17/17* | (2006.01) |
| *A61B 34/10* | (2016.01) |
| *A61B 90/00* | (2016.01) |
| *A61B 17/00* | (2006.01) |

(52) U.S. Cl.
CPC ........ *A61F 2/4612* (2013.01); *A61B 17/1778* (2016.11); *A61B 2017/00991* (2013.01); *A61B 2034/102* (2016.02); *A61B 2034/108* (2016.02); *A61B 2090/061* (2016.02); *A61F 2002/4627* (2013.01)

(58) Field of Classification Search
CPC .................. A61F 2/4612; A61B 17/1778
See application file for complete search history.

(56) References Cited

U.S. PATENT DOCUMENTS

| | | | | |
|---|---|---|---|---|
| 8,747,418 | B2 * | 6/2014 | Qureshi ................. | F16M 11/14 606/130 |
| 8,801,725 | B2 * | 8/2014 | Ritter .................... | A61B 17/17 606/102 |
| 8,926,627 | B2 | 1/2015 | Iannotti et al. | |
| 9,198,732 | B2 * | 12/2015 | Iannotti .............. | A61B 17/1739 |
| 9,717,508 | B2 | 8/2017 | Iannotti et al. | |
| 9,741,263 | B2 | 8/2017 | Iannotti et al. | |
| 10,028,803 | B2 * | 7/2018 | O'Neill .................. | A61B 90/50 |
| 2015/0190151 | A1 | 7/2015 | Budhabhatti et al. | |
| 2016/0242933 | A1 | 8/2016 | Deransart et al. | |

(Continued)

FOREIGN PATENT DOCUMENTS

| | | |
|---|---|---|
| CA | 2732836 | 2/2010 |
| CN | 102123677 | 7/2011 |
| EP | 2323582 | 5/2011 |

(Continued)

*Primary Examiner* — Zade Coley
(74) *Attorney, Agent, or Firm* — Karish & Bjorgum, PC

(57) ABSTRACT

The invention provides an adjustable pin setting targeter device for body tissue. It has an elongate longitudinal landmark guiding structure with a body with a through hole formed therethrough, a plurality of grooves formed on the body, a unique identifier associated with each groove, and a plurality of incremented number series equal to a number X next to each groove. Each incremented number series consists of a plurality of spaced apart incremented numbers N incremented by the number X, and associated location marks. The targeter devices also includes a plurality of legs that slideably engage with each groove, and a locking mechanism. Each leg has X number of longitudinally spaced apart unique identifiers and associated sight lines formed thereon. Each leg's longitudinal position is set by aligning one of its respective unique identifiers and its associated sight lines with one number N and associated location mark.

19 Claims, 14 Drawing Sheets

(56) References Cited

U.S. PATENT DOCUMENTS

2017/0079742 A1* 3/2017 O'Neill .................. A61B 90/50

FOREIGN PATENT DOCUMENTS

| EP | 2836136 | 2/2015 |
| EP | 3068317 | 8/2018 |
| JP | 2012500031 | 1/2012 |
| WO | 2010017641 | 2/2010 |
| WO | 2013152102 | 10/2013 |

* cited by examiner

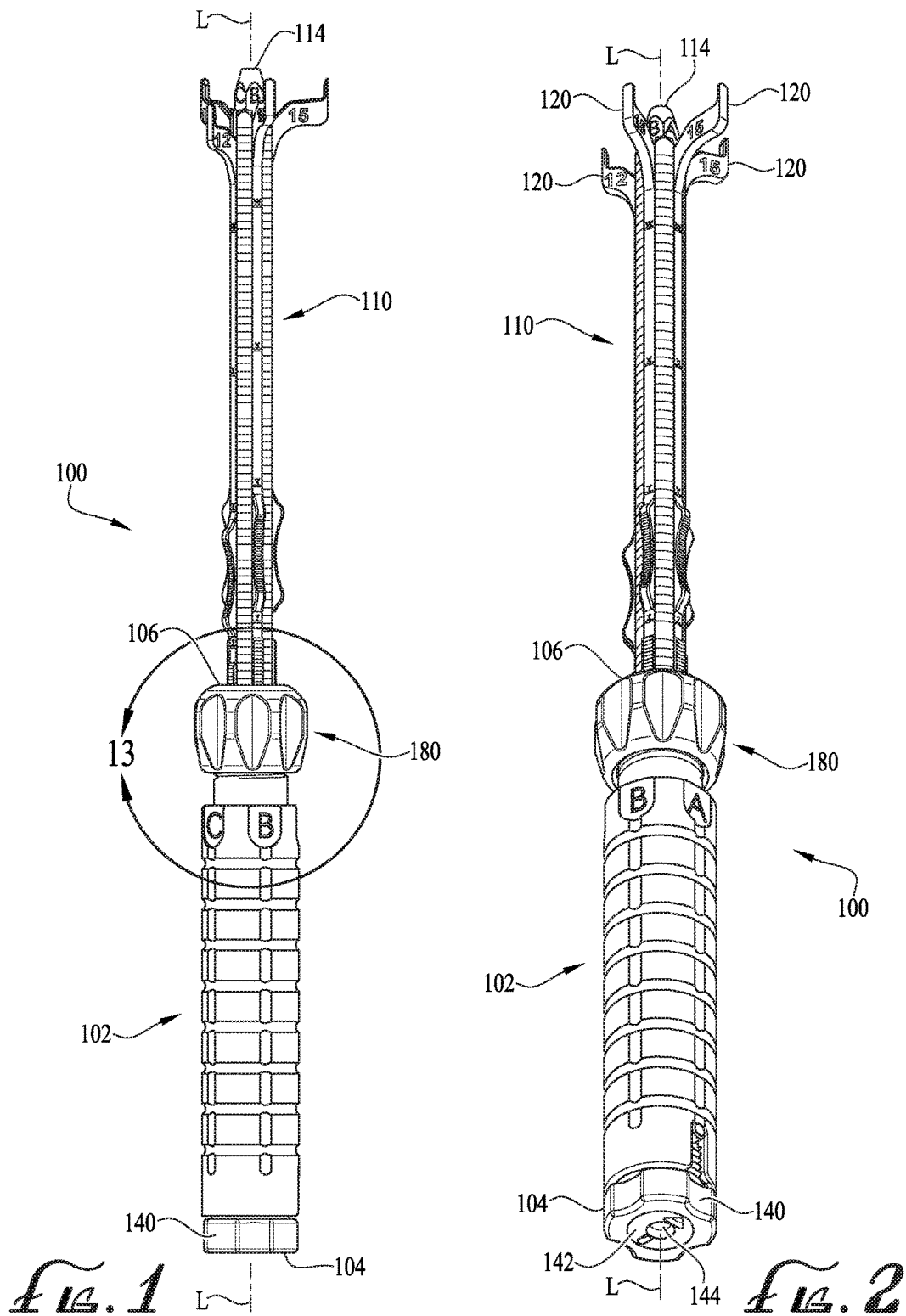

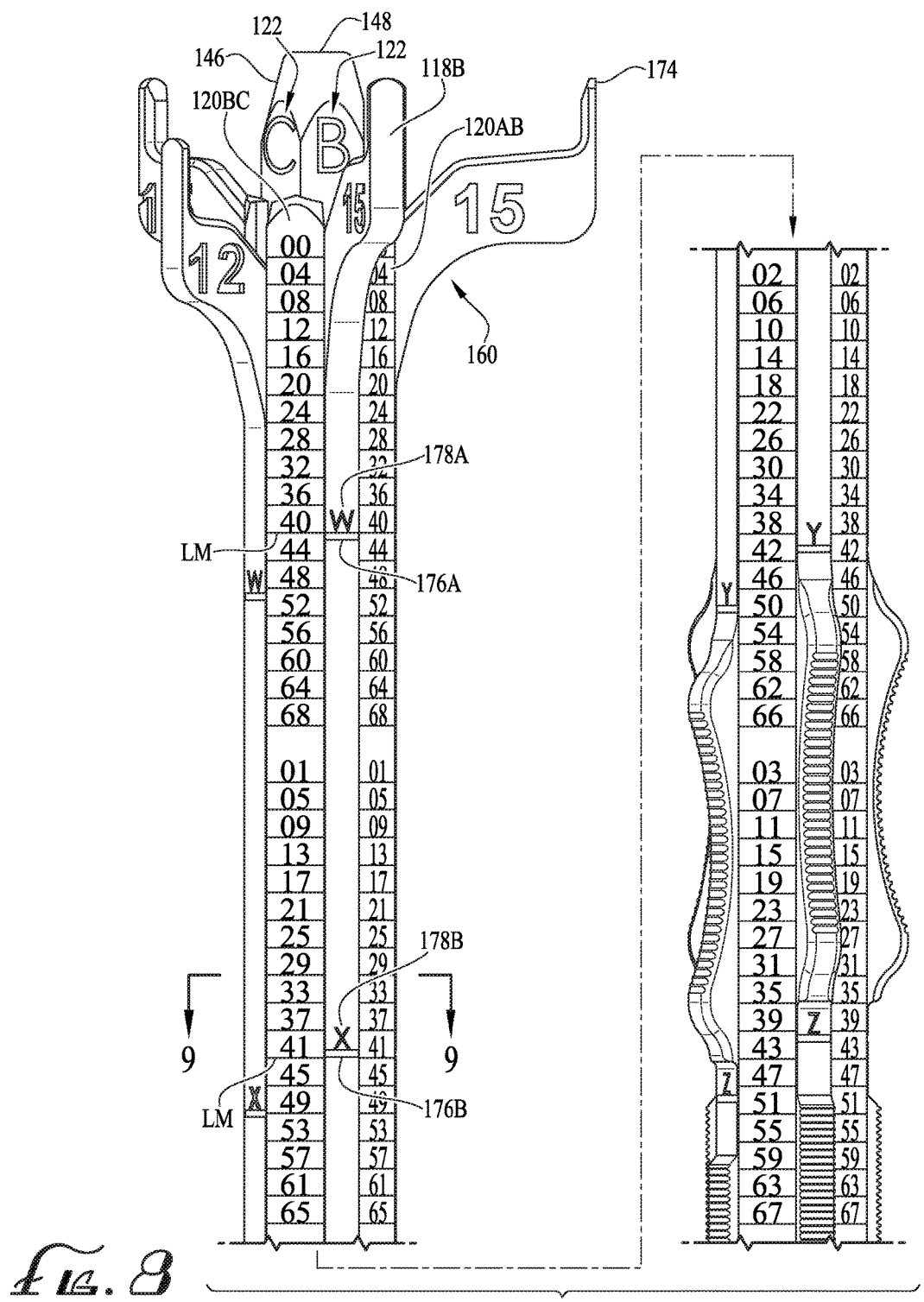

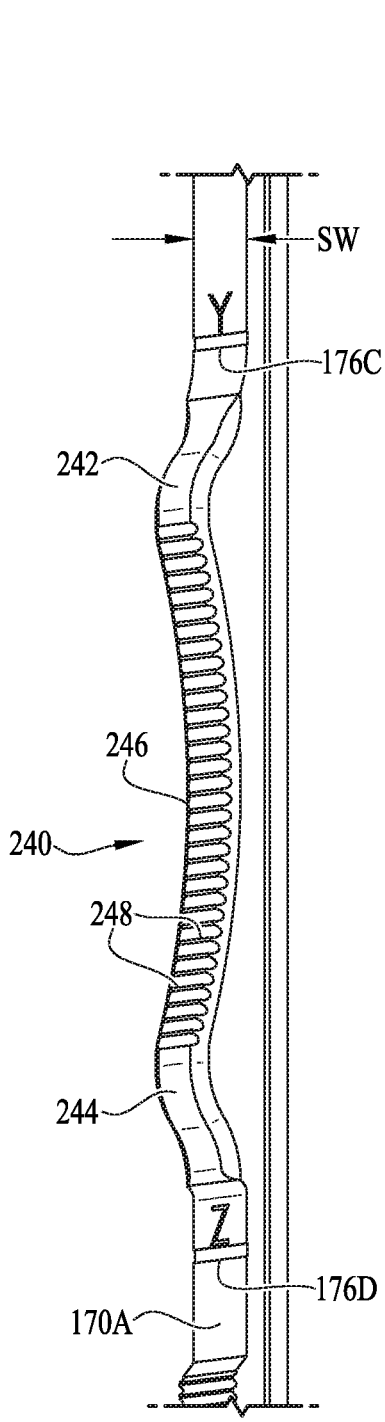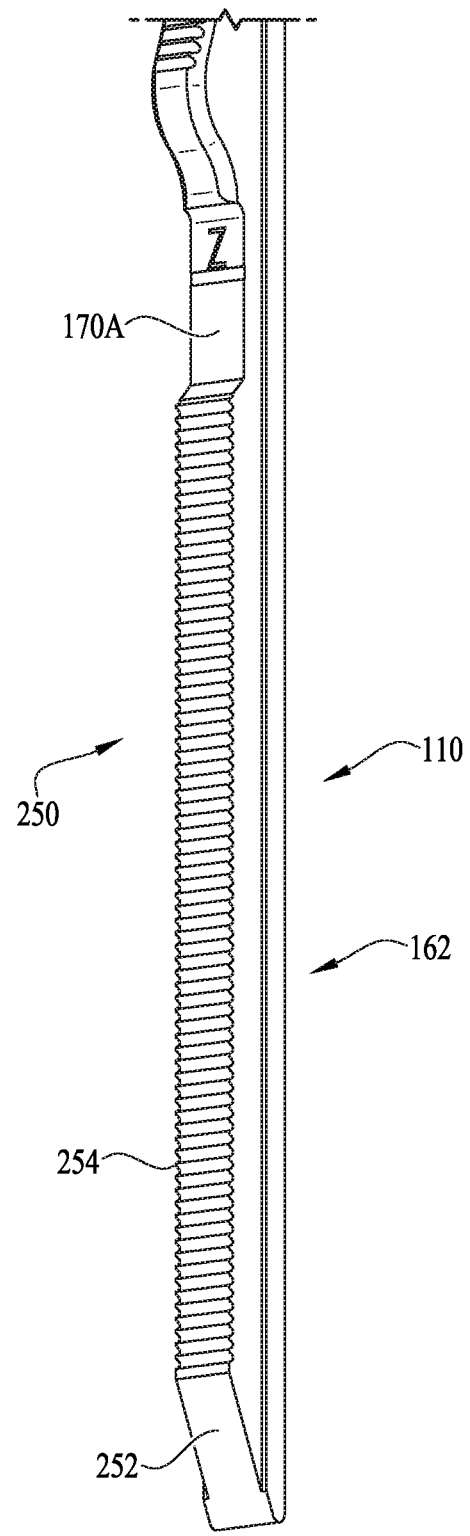

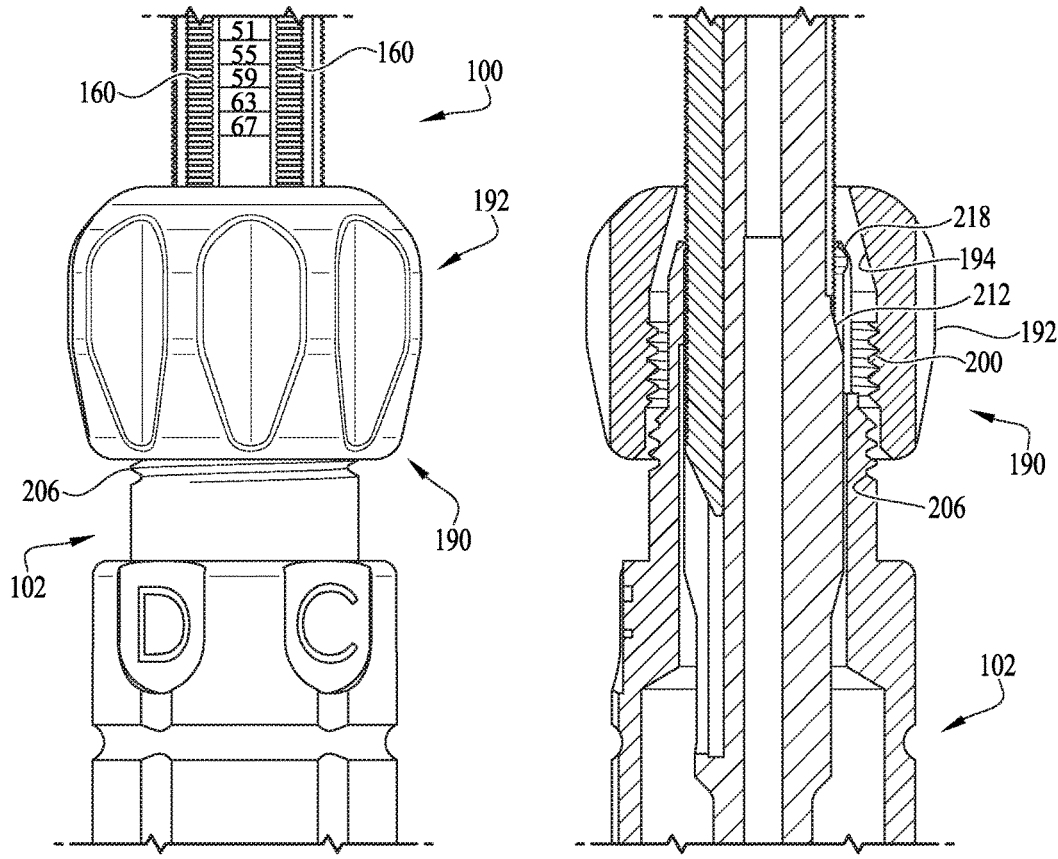
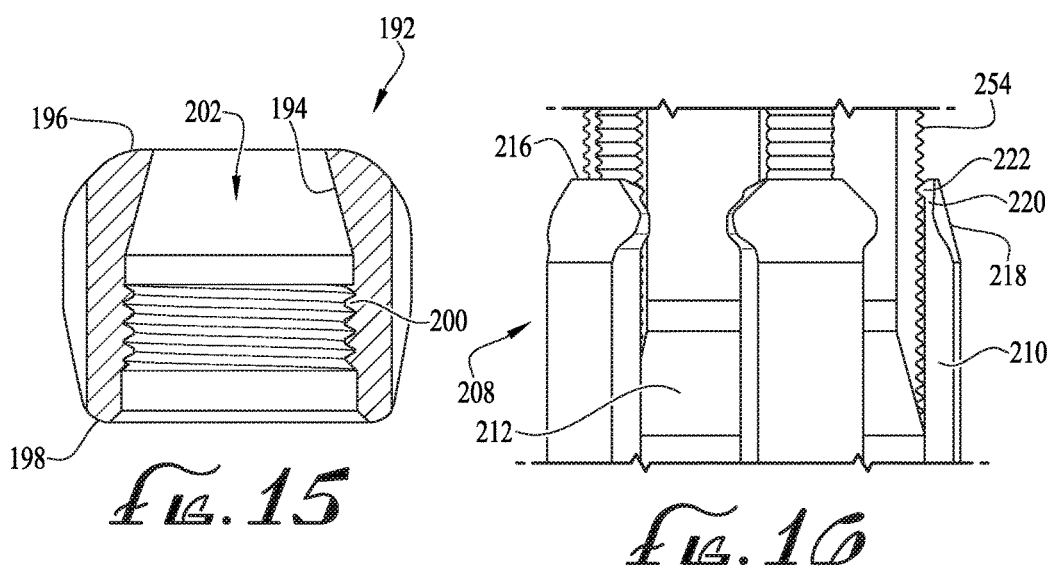

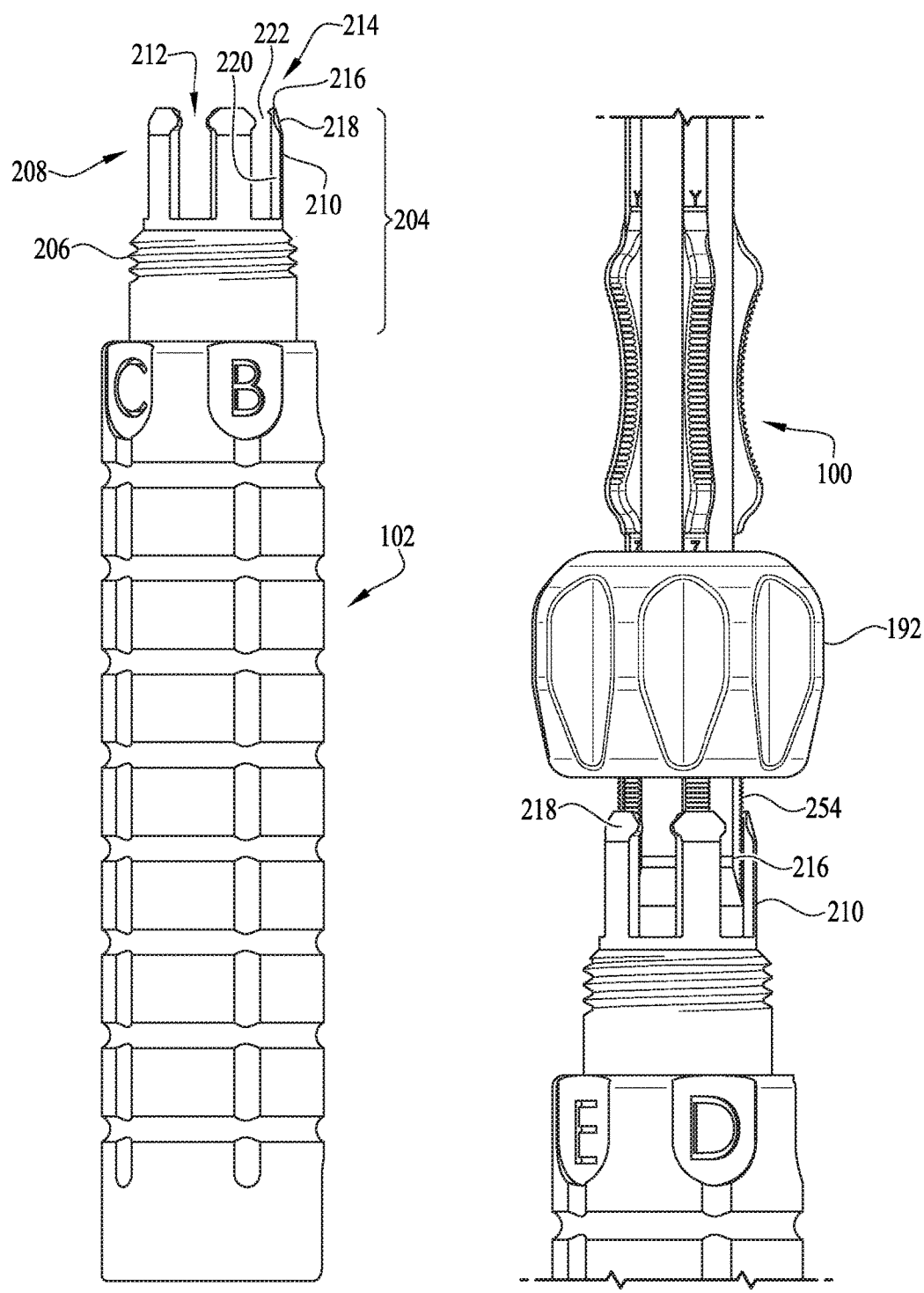

ADJUSTABLE PIN SETTING TARGETER DEVICE

FIELD OF THE INVENTION

The invention relates to devices and methods for setting an adjustable pin guide for location and trajectory to a patient's unique target tissue surface (e.g., bone) directly from settings prescribed by user software without the use of a secondary calibrator device and without use of a model of the target tissue surface.

BACKGROUND OF THE INVENTION

In the installation of prosthetics, accurate placement of the prosthetic relative to the implantation site is important to ensure proper connection and good biomechanics. For example, when installing a prosthetic shoulder joint into a patient's body, a glenoid component is implanted into the glenoid vault of the patient's scapula. An obverse surface of the glenoid component is configured for articulating contact with a humeral component carried by the patient's humerus. A reverse surface of the glenoid component is secured to the bone surface of the glenoid vault. Therefore, to ensure the best outcome, the glenoid component must be positioned accurately.

Presurgical planning is helpful to the surgeon and operating team as it aids the team in not only selecting the properly sized implant, but also helps the surgery go smoothly and without unnecessary surprises. This process is assisted by preoperative imaging and appropriate software. Modern presurgical planning results in a virtual surgical plan that is optionally at least partially embodied in a physical model of the patient's surgical site. This physical model is for example made by scanning the patient's surgical site and producing the physical model by 3-D printing or other technologies. This patient specific physical model will allow the surgeon to interact with model and glean useful information when developing the surgical plan.

One common use for the patient specific physical model is for calibrating or setting an adjustable surgical guide or placement instrument to prepare the surgical field to receive the prosthetic, e.g., by setting the location and placement of holes, bores, cuts, and the like.

Currently, tool setting devices are available to set adjustable surgical guides. However, it would be desirable to be able to transfer numerical setting from presurgical planning software directly to an adjustable surgical instrument without needing to use a physical patient surgical site model and without needing to use of a tool setting device.

SUMMARY OF THE INVENTION

The present invention is an adjustable pin setting targeter device for body tissue, comprising: an elongate longitudinal landmark guiding structure having a body with a longitudinal through hole formed therethrough, a plurality of longitudinal slide engagements formed on the body, a unique identifier associated with each longitudinal slide engagement, a plurality of incremented number series equal to a number X wherein the incremented number series are located adjacent to the longitudinal slide engagements, each incremented number series consisting of a plurality of incremented numbers N and associated location marks, wherein in the incremented number series each of the incremented numbers N are incremented from a lowest number to a highest number by the number X, wherein all adjacent location marks associated with incremented numbers N are spaced apart by a distance NS, and wherein the location marks associated with a first number and a last number of each number series are spaced apart by a distance L, and wherein adjacent incremented number series are separated by a distance NSD measured from the location marks associated with the last number and the first number of adjacent incremented number series, and wherein the first number and each subsequent number in each of the incremented number series is increased by one starting from the first incremented number series near the distal end of the elongate longitudinal landmark guiding structure and progressing to each subsequent incremented number series until the X numbered incremented number series is reached; and a plurality of elongate leg members, wherein each leg member is slidably engaged with the longitudinal slide engagements of the elongate landmark guiding structure, each elongate leg member having X number of longitudinally spaced apart unique identifiers and associated sight lines formed thereon which unique identifiers and associated sight lines are visible when the leg members are slidably engaged with the longitudinal slide engagements, wherein the X number of unique identifiers and associated sight lines are separated by a distance D equal to the distance L+the distance NSD−1/X of the distance NSD; whereby by sliding each leg member to align with one respective unique identifier and its associated sight line on that leg member with one number in one of the plurality of incremented number series in a respective longitudinal slide engagement, desired longitudinal positions of each leg members can be set.

The invention also provides an adjustable pin setting targeter device for body tissue, comprising: an elongate longitudinal landmark guiding structure having a body with a longitudinal through hole formed therethrough, a plurality of longitudinal grooves formed on the body, a unique identifier associated with each longitudinal slide engagements, a plurality of incremented number series equal to a number X wherein the incremented number series are located adjacent to the grooves, each incremented number series consisting of a plurality of incremented numbers N and associated location marks, wherein in the incremented number series each of the incremented numbers N are incremented from a lowest number to a highest number by the number X, wherein all adjacent location marks associated with incremented numbers N are spaced apart by a distance NS, and wherein the location marks associated with a first number and a last number of each number series are spaced apart by a distance L, and wherein adjacent incremented number series are separated by a distance NSD measured from the location marks associated with the last number and the first number of adjacent incremented number series, and wherein the first number and each subsequent number in each of the incremented number series is increased by one starting from the first incremented number series near the distal end of the elongate longitudinal landmark guiding structure and progressing to each subsequent incremented number series until the X numbered incremented number series is reached, and wherein the elongate longitudinal landmark guiding structure connects to the handle with its distal end extending outwardly therefrom; a plurality of elongate leg members, wherein each leg member is slidably engaged with the longitudinal grooves of the elongate landmark guiding structure, each elongate leg member having X number of longitudinally spaced apart unique identifiers and associated sight lines formed thereon which unique identifiers and associated sight lines are visible when the leg members are slidably engaged with the longitudinal grooves, wherein the X number of unique identifiers and associated sight lines are separated by a distance D equal to the distance L+the distance NSD−1/X of the distance NSD; and a locking mechanism to lock in the longitudinal position of the plurality of elongate leg members in the longitudinal slide engagements of the elongate landmark guiding structure; whereby by sliding each leg member to align with one respective unique identifier and its associated sight line on that leg member with one number in one of the plurality of incremented number series in a respective longitudinal slide engagement, desired longitudinal positions of each leg members can be set.

The invention further provides an adjustable pin setting targeter device for body tissue, comprising: an elongate longitudinal landmark guiding structure having a body with a longitudinal through hole formed therethrough, a plurality of longitudinal grooves formed on the body, a unique identifier associated with each longitudinal slide engagements, a plurality of incremented number series equal to a number X wherein the incremented number series are located adjacent to the grooves, each incremented number series consisting of a plurality of spaced apart incremented numbers N and associated location marks, and wherein the elongate longitudinal landmark guiding structure connects to the handle with its distal end extending outwardly therefrom; a plurality of elongate leg members, wherein each leg member is slidably engaged with the longitudinal grooves of the elongate landmark guiding structure, each elongate leg member having X number of longitudinally spaced apart unique identifiers and associated sight lines formed thereon which unique identifiers and associated sight lines are visible when the leg members are slidably engaged with the longitudinal grooves; and a locking mechanism to lock in the longitudinal position of the plurality of elongate leg members in the longitudinal slide engagements of the elongate landmark guiding structure; whereby by sliding each leg member to align with one respective unique identifier and its associated sight line on that leg member with one number in one of the plurality of incremented number series in a respective longitudinal slide engagement, desired longitudinal positions of each leg members can be set.

These and other features of the invention are described below.

BRIEF DESCRIPTION OF THE DRAWINGS

FIG. 1 is a front view of an exemplary embodiment of a pin setting targeter device of the invention.

FIG. 2 is a first perspective view of the targeter device of FIG. 1.

FIG. 8 is an enlarged front view of the shaft region of the targeter device of FIG. 1 with the shaft region split into two sections and showing the leg members in place.

FIG. 11 is a detail perspective view showing a portion of the leg member in the area 11-11 of the leg member of FIG. 10B.

FIG. 12 is a detail perspective view showing a portion of the leg member in area 12-12 of FIG. 10B.

FIG. 13 is a front perspective detail view of the targeter device in the region 13-13 of FIG. 1.

FIG. 14 is a cross-section view of the region of the targeter device of FIG. 13, but with a compression nut further tightened down.

FIG. 15 is a cross-sectional view of the compression nut of FIG. 14.

FIG. 16 is detail side view showing the locking fingers on the handle engaging with locking teeth on the leg member.

FIG. 17 is a front view of the handle.

FIG. 18 is a front view showing the compression nut before it is tightened down on the locking fingers of the handle.

DETAILED DESCRIPTION

Figure 3:
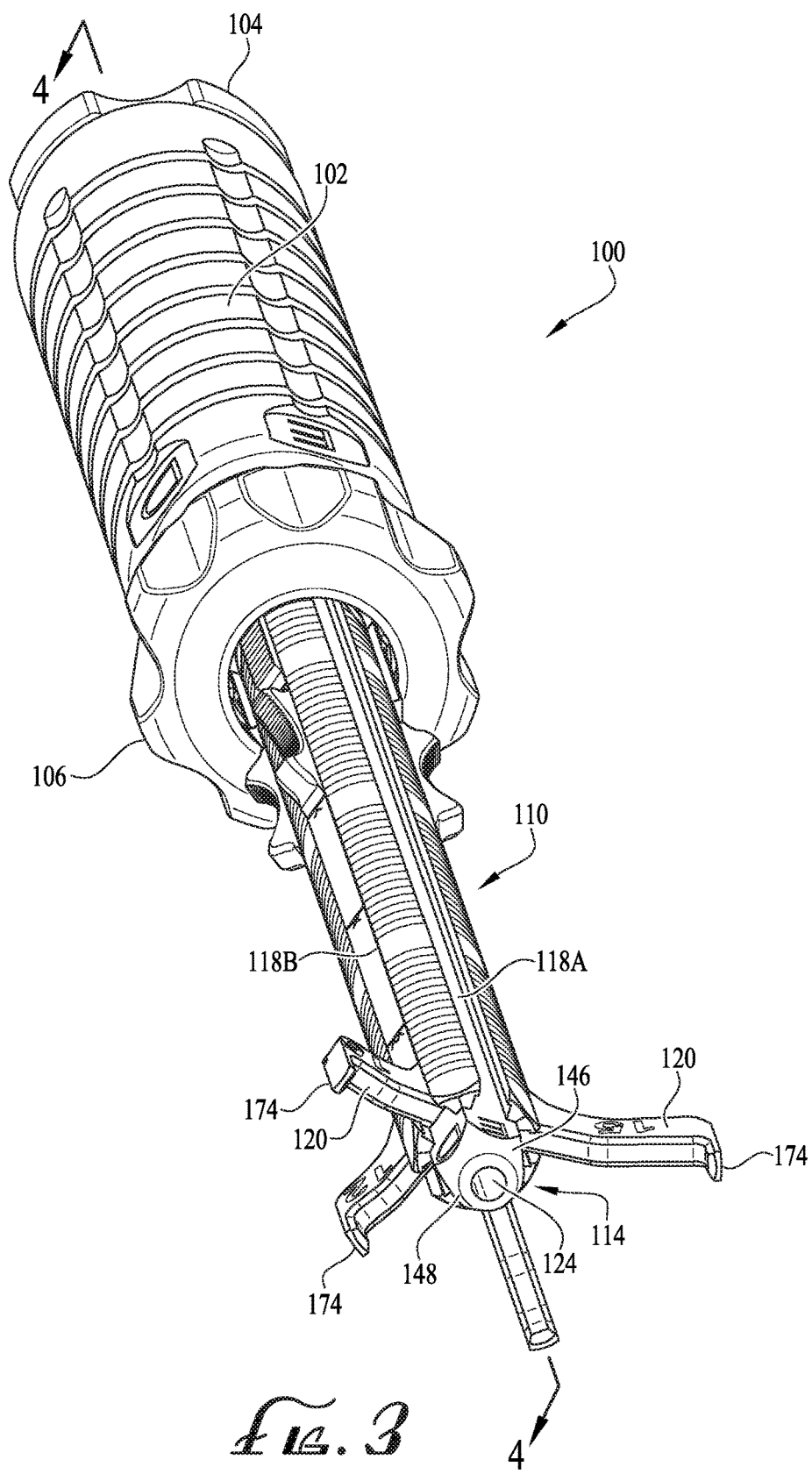
FIG. 3 is another perspective view of the targeter device of FIG. 1.
Figure 4:
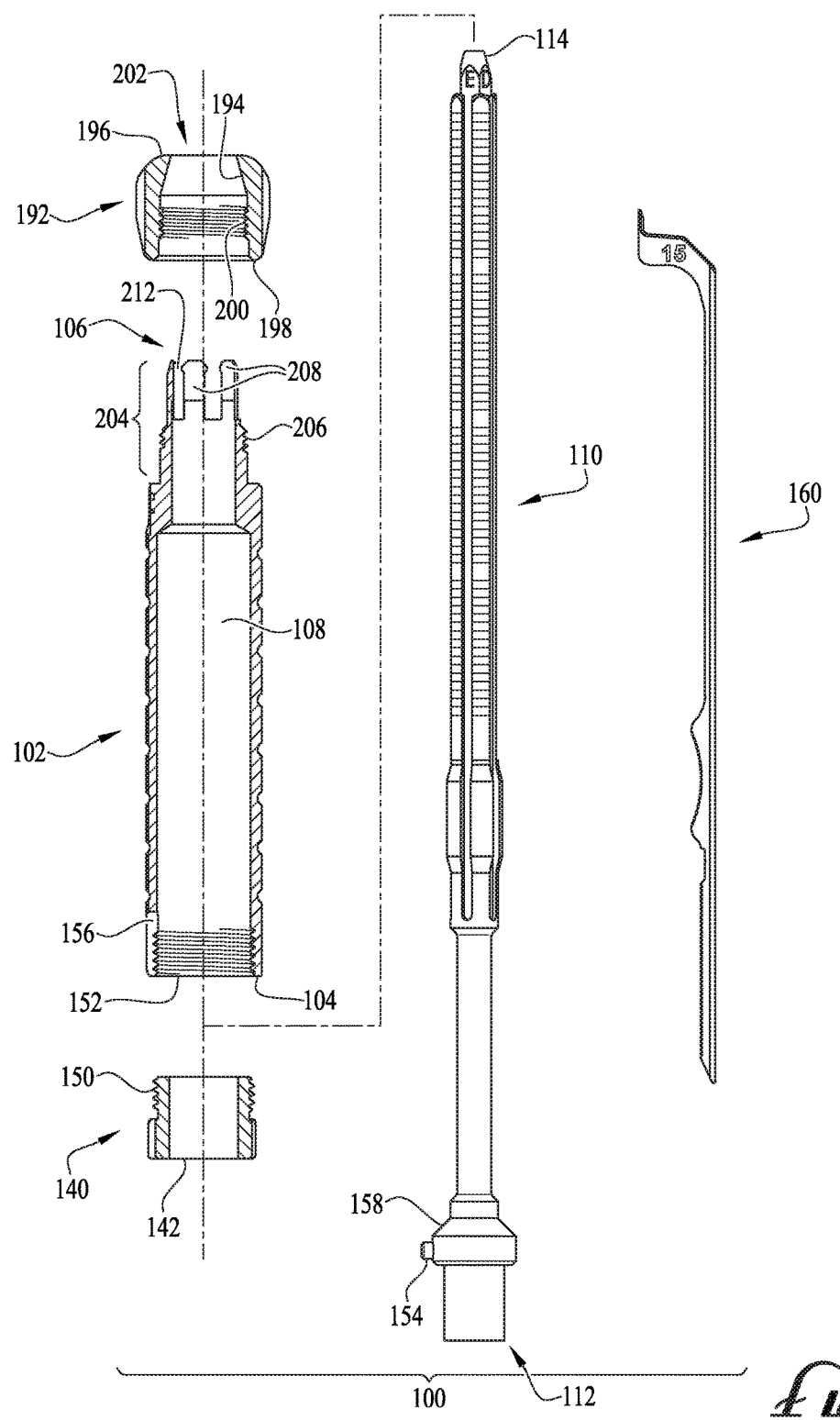
FIG. 4A is an exploded view of the targeter device of FIG. 1 showing certain components in cross-section.
FIG. 4B is longitudinal cross-section view of the targeter device of FIG. 1 along view lines 4-4 of FIG. 3.

Referring to FIGS. 1-3, there are shown views of an exemplary embodiment of an adjustable pin setting targeter device (also referred to herein as targeter device) 100 which is useful for setting a desired location and desired trajectory of a pin to be placed in a patient's unique targeted tissue at a surgical site. The exemplary embodiment of the adjustable pin setting targeting device 100 is particularly well adapted as a guide for preparing a surgical site to receive implantation of a prosthetic, e.g., to be used to place precisely located and angled holes for pins, screws and the like. In one embodiment, the targeting device 100 was developed for preparing the glenoid cavity of the scapula, but the targeting device 100 can be used for preparing other surgical sites of the body. The targeting device 100 preferably includes a handle 102 with a longitudinal axis L. The handle 102 has a proximal end 104 and a distal end 106. As best shown in FIGS. 4A and 4B, a channel 108 extends longitudinally along the longitudinal axis L through the handle 102 and passes through the distal end 106 of the handle 102. The targeting device 100 further includes an elongate landmark guiding structure 110 having a proximal end 112 and a distal end 114. The elongate landmark guiding structure 110 includes a shaft region 116 that extends outwardly from the distal end 114 of the handle 102. In the exemplary embodiment of the targeting device 100 described above, the handle 102 and the elongate landmark guiding structure 110 are separate pieces that are retained together. However, they could be formed in one piece, e.g. by 3-D printing.

Figure 6:
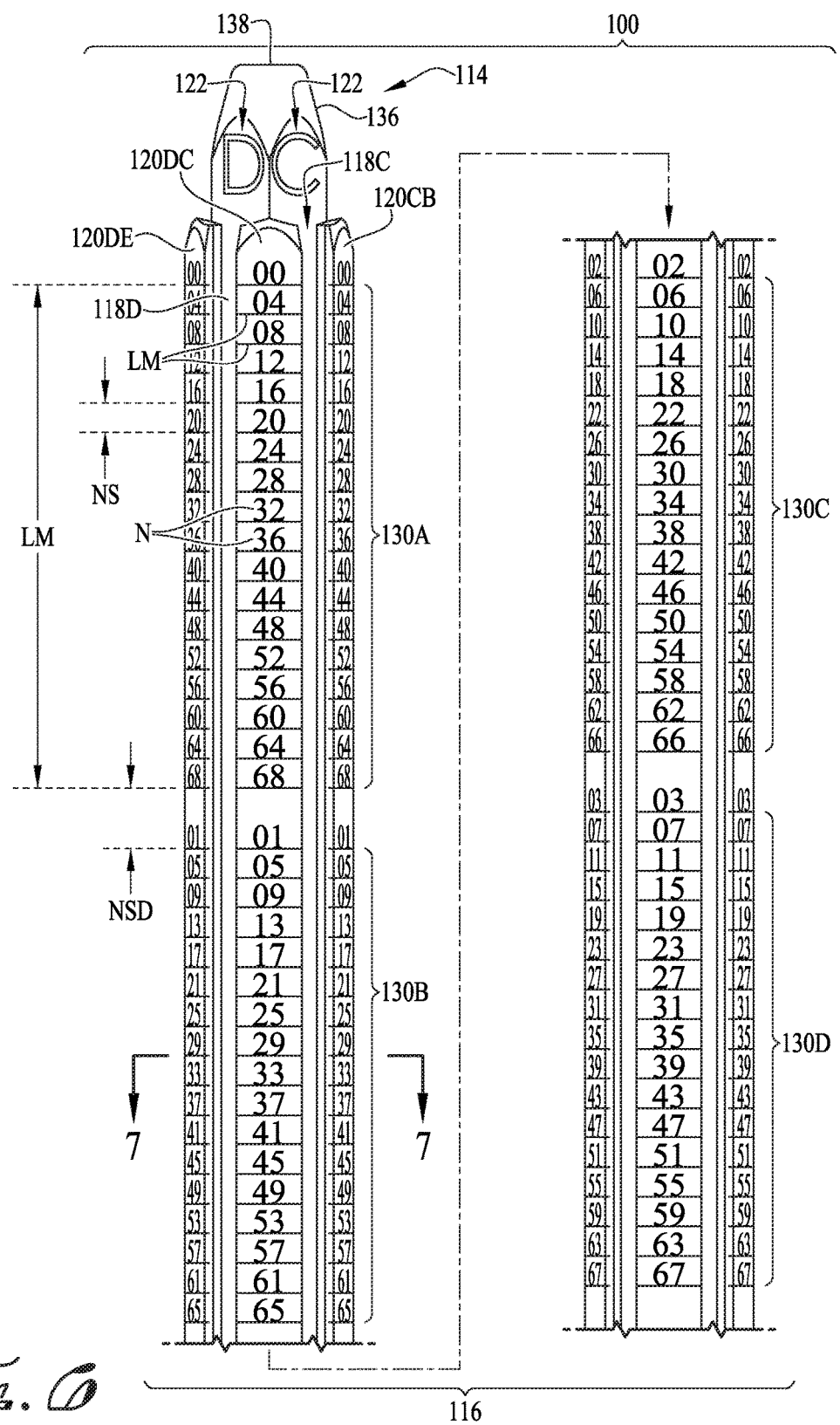
FIG. 6 is an enlarged front view of the shaft region of the targeter device of FIG. 5 with the shaft region split into two sections.
Figure 7:
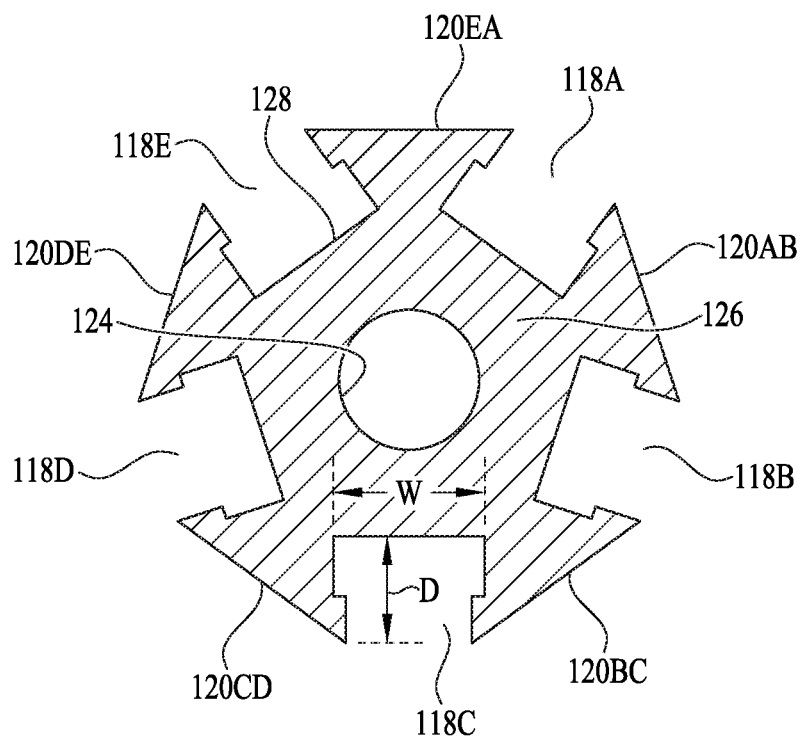
FIG. 7 is a cross-sectional view through view lines 7-7 of FIG. 6.

As best shown in FIGS. 6 and 7, the elongate landmark guiding structure 110 has a plurality of spaced apart longitudinal slide engagements 118A, 118B, 118C, 118D, 118E distributed around the elongate landmark guiding structure 110 and extended to the distal end 114 of the elongate landmark guiding structure 110. Although five slide engagements 118A-E are shown, a greater or lesser number of slide engagements can be provided. In the noted embodiment of the targeting device 100, the spaced apart longitudinal slide engagements 118A-E comprise elongate grooves, each having a predetermined width "W" and depth "D" that extend onto the elongate landmark guiding structure 110. In the exemplary embodiment 100, the grooves 118A-E are defined by pairs of scaled rulers 120AB-EA which straddle and define each of the grooves 118A-E. For example, groove 118D is defined by the straddling scaled rulers 120DE and 120CD, and groove 118C is defined by the straddling scaled rulers 120CD and 120BC, and so on. However, other slidable engagements can be used instead. Each slide engagement 118A-E has a unique identifier 122 associated therewith, such as a letter (e.g., A, B, C, D, and E), a number, a color, a symbol, or some other indicator to distinguish each slide engagement from each other slide engagements. In the embodiment shown, the unique identifier 122 for each slide engagements 118A-E is a letter A, B, C, D, and E, with letters D and C being shown.

Figure 5:
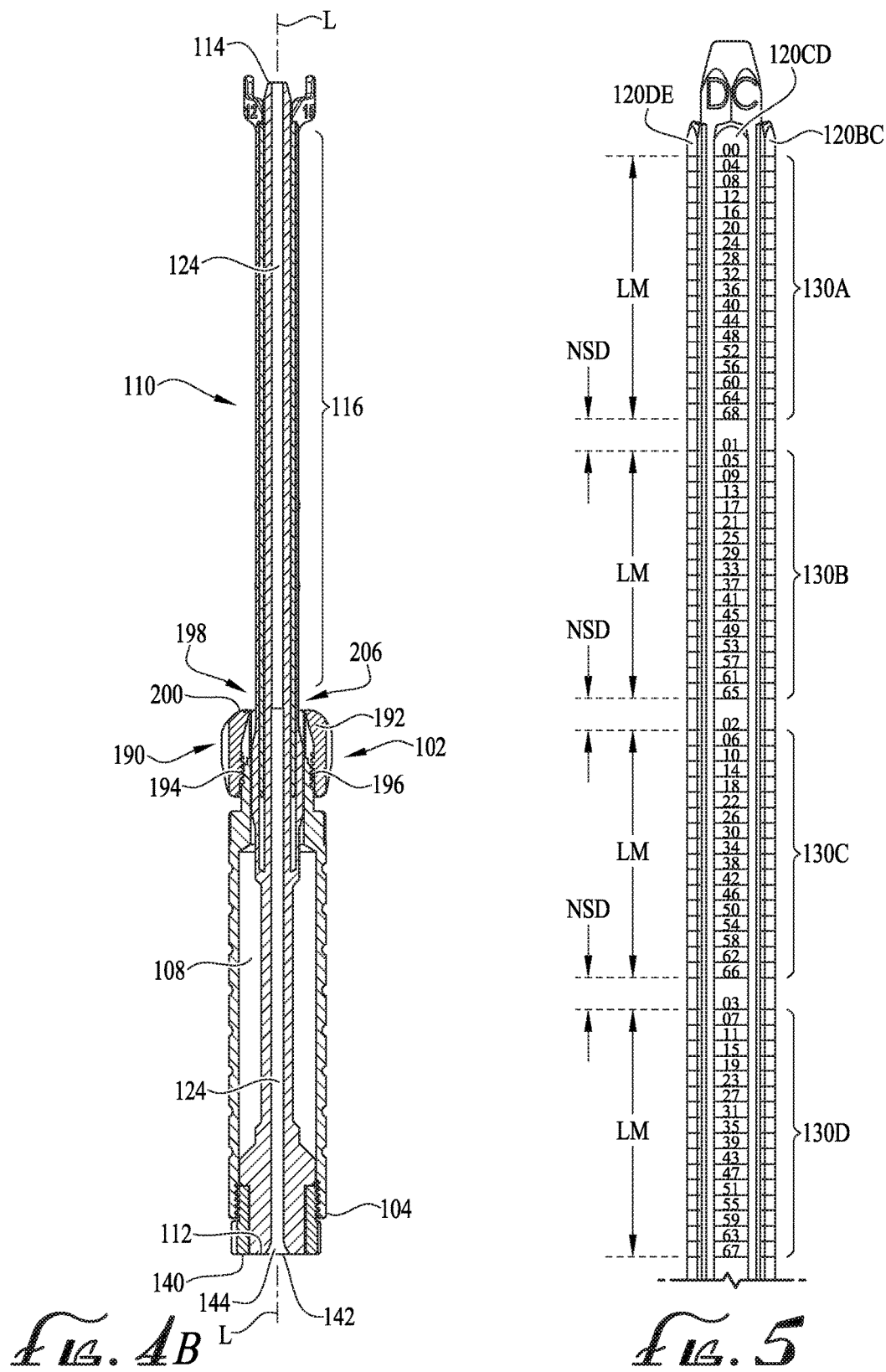
FIG. 5 is front view of the shaft region of the targeter device of FIG. 1 but without the leg members in place.
Figure 9:
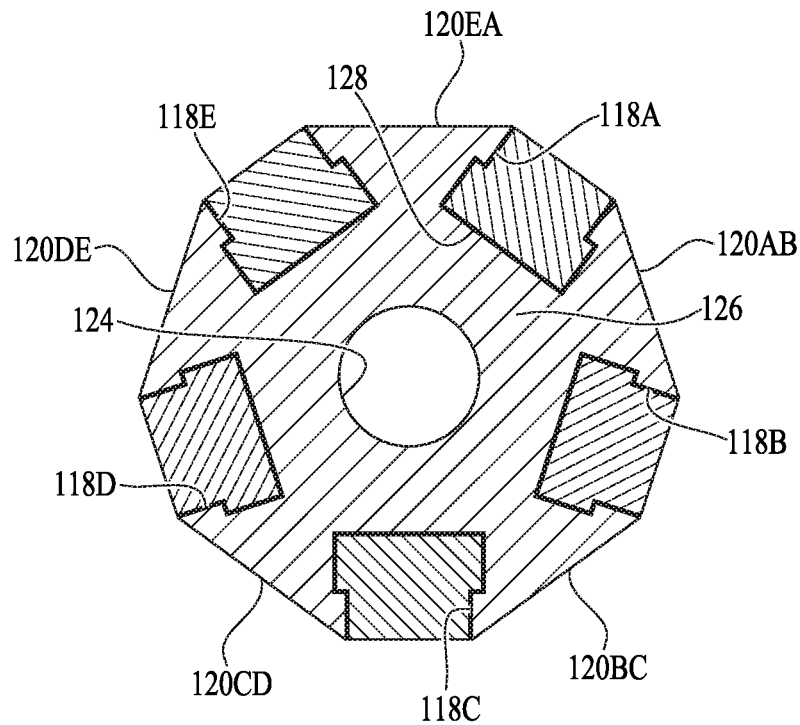
FIG. 9 is a cross-sectional view through view lines 9-9 of FIG. 8.
Figures 10A, 10B:
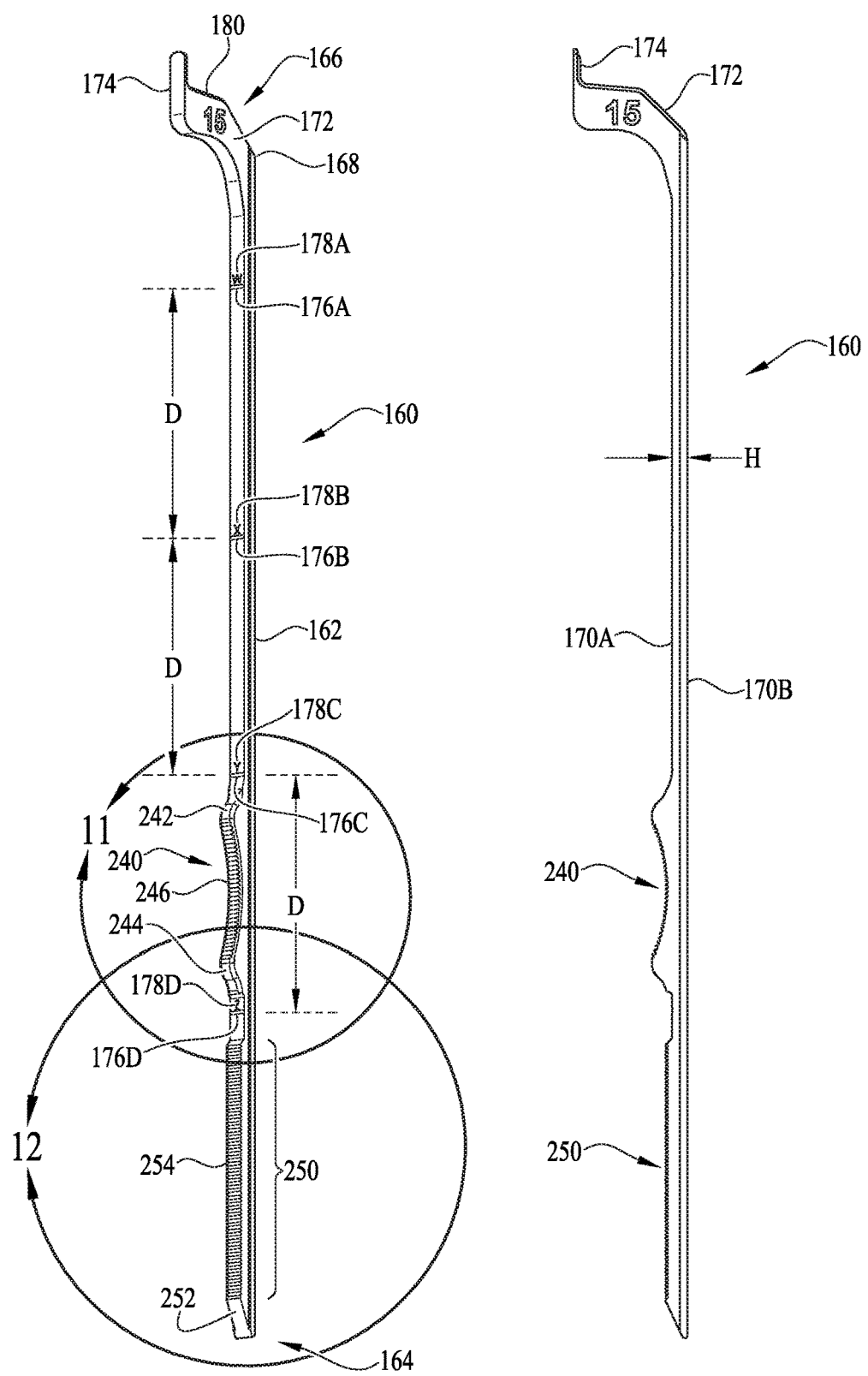
FIG. 10A is a perspective view of a leg member of the invention.
FIG. 10B is a side view of the leg member of FIG. 10A.
Figures 10C, 10D:
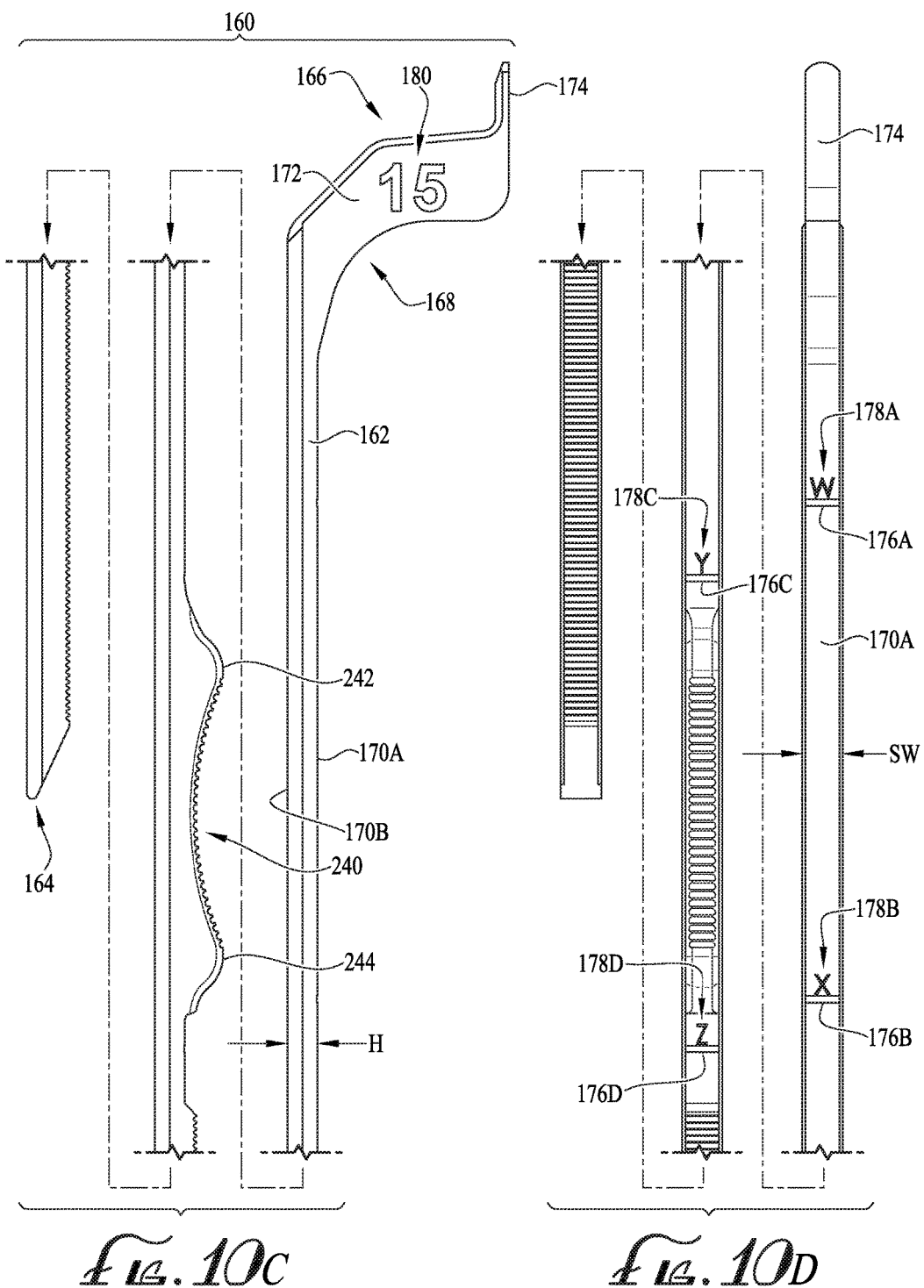
FIG. 10C is a side view of the leg member of FIG. 10A but split into three sections to show greater detail.
FIG. 10D is a front view of the leg member of FIG. 10A but split into three sections to show greater detail.

As best shown in FIGS. 4B, 7 and 9, the elongate landmark guiding structure 110 includes a through bore 124 that passes longitudinally from the proximal end 112 to a distal end 114 through a center body 126 of landmark guiding structure 110. The through bore 124 has an entrance 144 at its proximal end 112. A bottom 128 of each groove 118A-E thus can be the outside surface of the center body 126 between each pair of straddling scaled rulers 120AB-EA. The through bore 124 is, for example, adapted for passage of a drill or boring tool. The elongate landmark guiding structure 110 can be made of rigid plastic, metal or other materials and the scaled rulers 120AB-EA can be formed together with the center body 126, or can be attached by other means. FIGS. 5, 6 and 8 show the scaled rulers 120AB-EA, each having a series of incremented numbers "N" located thereon. In the embodiment shown, there are four (4) series of incremented numbers aligned vertically on the scaled rulers 120AB-EA, namely number series 130A, 130B, 130C, and 130D. In the embodiment shown, there are 18 separate numbers "N" in each number series 130A, 130B, 130C, and 130D, with the numbers in each number series being incremented by four (4) going from the number in the first position as each consecutive number progresses down to the 18$^{th}$ number in each number series from the distal end to the proximal end of the scaled rulers 120AB-EA. Furthermore, starting from the first number in each number series 130A, 130B, 130C, and 130D, each number in the same place is incremented higher by one digit. For example, number series 130A comprises the following numbers, each number being vertically aligned and being underlined with a location marker line "LM" so as to provide a line associated with each number: 00, 04, 08, 12, 16, 20, 24, 28, 32, 36, 40, 44, 48, 52, 56, 60, 64, and 68. The next number series 130B on the scaled rulers 120A-E comprises the following numbers, each also being underlined with the location marker "LM": 01, 05, 09, 13, 17, 21, 25, 29, 33, 37, 41, 45, 49, 53, 57, 61, 65, and 69. Series 130C which is located below number series 130B comprises the following numbers, each being underlined with the location marker line "LM": 02, 06, 10, 14, 18, 22, 26, 30, 34, 38, 42, 46, 50, 54, 58, 62, 66, and 70. The last number series 130D is located below number series 130C and comprises the following numbers, each being underlined with the location marker "LM": 03, 07, 11, 15, 19, 23, 27, 31, 35, 39, 43, 47, 51, 55, 59, 63, 67, and 71. Thus, taking in account all of the numbers series in each scaled rulers, all number from 00 to 71 are presented on each scaled rulers 120A-E, but in the order as noted above. Each of the scaled rulers 120AB-EA are positioned such that the same numbers on each scaled rulers 120AB-EA are aligned across all of the grooves 118A-E. The distance or spacing "NS" between each incremented number and its associated location marker line "LM" in each number series 130A-D is the same. In the exemplary embodiment this can be for example 2 mm. Thus, there is provided enough space to have the number associated with each location marker line to be presented in a small, albeit legible font. With a 2 mm spacing between each unique number N and location marker "LM" in each number series 130A-D, the length "L" of each number series between the first and last location marker lines "LM" is "L"=2 mm×17=34 mm. A number series is separated by the next adjacent numbers series by a distance "NSD" that is preferably greater than the distance between each number in a number series, for example by 4 mm. This distance "NSD" will create a visual break that helps users distinguish between each number series 130A, 130B, 130C and 130E.

As noted above, the elongate landmark guiding structure 110 is positioned in the channel 108 of the handle 102 such that the shaft region 116 extends beyond the distal end 106 and with the proximal end 112 of the elongate landmark guiding structure 110 being adjacent to the proximal end 104 of the handle 102. As shown in FIGS. 1, 2 and 4A and 4B, a cap 140 is used to cap off the proximal end 104 of the handle 102. In one embodiment, the cap 140 has an externally threaded end 150 which threads into a complementary internally threaded end 152 of the handle 102. A set screw 154 passes through a screw hole 156 in the handle 102 and screws into a retainer 158 near the proximal end of the elongate landmark guiding structure 110 to retain the elongate landmark guiding structure 110 in the handle 102 in a desired position. However, the cap 140 can be engaged with the handle 102 by various other known attachments, including but not limited to having other screw fits with the handle 102, snapping on, gluing in place, friction fitting in place, welding in place, etc. In lieu of using a cap 140 to retain the landmark guiding structure 110 in the channel 108 of the handle 102, the landmark guiding structure 110 could itself be snap fitted within the channel, be glued or welded in place, screwed in place, and be retained in place by holding devices such as screws, pin, or other holding devices. The cap 140 is opened at its end 142 to expose the entrance 144 of the through bore 124 that passes through the landmark guiding structure 110. Thus, a drill or other boring tool (not shown) can be passed through the entrance 144 of the through bore 124 and out the distal end 114 of the elongate landmark guiding structure 110. As best shown in FIG. 3, the distal end 114 of the elongate landmark guiding structure 110 can preferably have a narrowed down beveled end 146 where the through bore 124 exits the distal end 114 forming a narrow rim tip 148 around the through bore 124 that exits the distal end 114. In use of the targeting device 100, the narrow rim tip 148 will be placed on the surgical site with the through bore 124 aligned with a desired location on the surgical site.

Referring to FIGS. 10A-10D, 11 and 12, each leg member 160 includes an elongate strip portion 162 with a proximal end 164 and a distal leg portion 166 located at a distal end 168 of the leg member 160. Each elongate strip portion 162 has a top edge 170A and a bottom edge 170B. The distal leg portion 166 includes an extension portion 172 extending away from the elongate strip portion 162. A terminal foot 174 is at an end of the extension portion 172 and points out distally and can have a variety of profiles, such as a sharp point, a flat blade shape, or other desired shapes. In use, the terminal feet 174 of each leg member 160 will be placed on the surgical site. The terminal feet 174 are laterally spaced away from the elongate strip portions 162. The elongate strip portions 162 have a width "SW", a height "H", and a length, where the width "SW" is smaller than the width "W" of the grooves 118A-E to allow sliding motion of the elongate strip portion 142 of the leg members 140 in the grooves 118A-E, and wherein the height "H" of the elongate strip portions 142 is greater than the depth "D" of the grooves 118A-E, so that when elongate strip portions 142 of the leg members 140 are placed in the grooves 118A-E with the bottom edges 170B placed against the bottom of the groove 118A-E, the top edge 170A will extend beyond the outer surfaces of the scaled rulers 120AB-EA, as shown for example in FIGS. 9 and 16. Located on the top edge 170A of each elongate strip portion 162 are a series of spaced apart horizontally arranged sight lines 176A, 176B, 176C and 176D, and associated unique identifiers 178A, 178B, 178C and 178D, wherein the unique identifiers can for example be letters, numbers, other symbols, colors, shapes, etc. In the embodiment described, the unique identifiers 178A, 178B, 178C and 178D are the numbers W, X, Y and Z, respectively, arranged with the letter "W" closer to the distal end 168 of each leg members 160, then with letter X, then Y and finally letter Z located closest to the proximal end 164 of each leg member 160. Each leg portion 160 will also preferably bear a leg type indicator 180, shown here as a large number "15". The leg indicator 180 can be used to identify the leg portion as having a particular combination of extension portions 172 and/or terminal foot 174. Each of the plurality of elongate leg members 160 can be identical or can be different in terms of their extension portions 172 and/or terminal feet 174.

In this embodiment with four number series 130A, 130B, 130C, and 130D on the elongate longitudinal guiding structure, the distance "D" between adjacent pairs of horizontally arranged tracking lines 176A and 176B, 175B and 176C, and 176C and 176D will be equal to the distance between the first and last location marker "LM" in a number series (e.g., 120A) plus the distance "NSD" that separates adjacent number series minus one quarter (¼) of the distance two adjacent location markers "LM". In the example given, this equals (2 mm*17) (the distance between the first and last location marker "LM" in a number series)+4 mm (the distance "NSD" that separates adjacent number series)– (0.25*2 mm) (¼ of distance two adjacent location markers "LM")=35.5 mm. Thus, when for example on a single leg members 160 the unique identifiers 178A (e.g., the letter W) is positioned with its sight line 176A aligned with location marker "LM" associated with the number 40, the unique identifiers 178B (letter X) will be positioned with its sight line 176B positioned ¼ (one quarter) of the way above the location marker "LM" associated with the number 41 and ¾ (three quarters) of the way below the location marker "LM" associated with number 37, the unique identifiers 178C (letter Y) will be positioned with its sight line 176C positioned ½ (one half) of the way above the location marker "LM" associated with the number 42 and ½ (one half) of the way below the location marker "LM" associated with number 38, and unique identifiers 178D (letter Z) will be positioned with its sight line 176D positioned ¾ (three quarters) of the way above the location marker "LM" associated with the number 43 and ¼ (one quarter) of the way below the location marker "LM" associated with number 39. Therefore, if the single leg members 160 were to be slid rearwardly so that unique identifier 178B (letter X) is aligned with its sight line 176A positioned in line with the location marker LM associated with the number 41, this would result in the single leg members 160 moving ¼ (on quarter) of the distance of the number spacing "NS" between adjacent numbers. As previously described, this equates to 0.5 mm longitudinal movements that can be accurately made and easily seen by users. If a user wishes to slide a single leg member 160 rearwardly by 1 mm, then the user would align the sight line 176C of unique identifier 178C (letter Y) in position with the location marker "LM" associated with the number 42, and if the user wishes to slide a single leg members 160 rearwardly by 1.5 mm, then the user would align the sight line 176D of unique identifier 178D (letter Z) in position with the location marker "LM" associated with the number 43. In order to make it easier for a user to slide each leg member 160 within its groove 118, a thumb grip 240 is preferably formed on the top edge 170A of the elongate landmark guiding structure 110 and can be in the form of two upraised arched portions 242 and 244 with a valley 246 between. For better grip, serrations 248 can be included on the top surface thereof. The thumb grip 240 will preferably be positioned between sight lines 176C (below letter "Y") and 176D (below letter "Z"). Located at the proximal most one-quarter end of the elongate strip portion 162 is a capture end 250. The capture end 250 can include a beveled terminal end 252 and a series of spaced apart engagements 254 on a top surface 170A thereof, such as spaced apart and horizontally oriented slots, ridges or teeth. The beveled terminal end 252 will make it easier to slide the elongate landmark guiding structure 110 into the handle 102 during assembly.

In the preferred embodiment described there are four number series 130A, 130B, 130C, and 130D (X=4), and the numbers in each number series are incremented by four (4), and there are likewise four unique identifiers 178A-D and associated sight lines 78A-D. If there were five number series (X=5), then the consecutive numbers in each number series would increment by five (5), and there would be five unique identifiers and associated sight lines. Thus, with the same spacing between each number N in a number series (e.g. 2 mm), instead of being able to set each leg member in 0.5 mm increments (=¼*2 mm), each leg member could be set in 0.4 mm increments (=⅕*2 mm) so greater accuracy could be provided.

Figure 19:
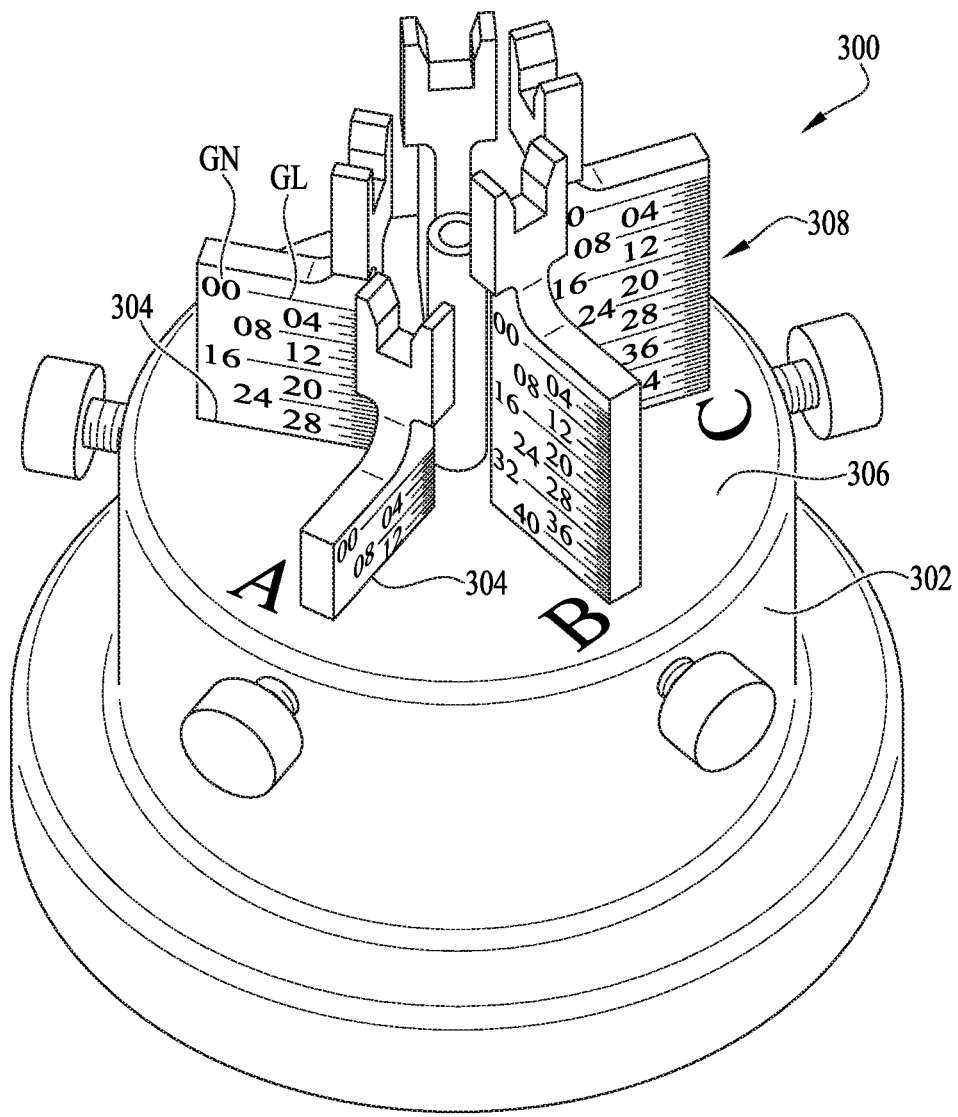
FIG. 19 is a perspective view of a prior art targeter device setting device.
Figures 20, 21:
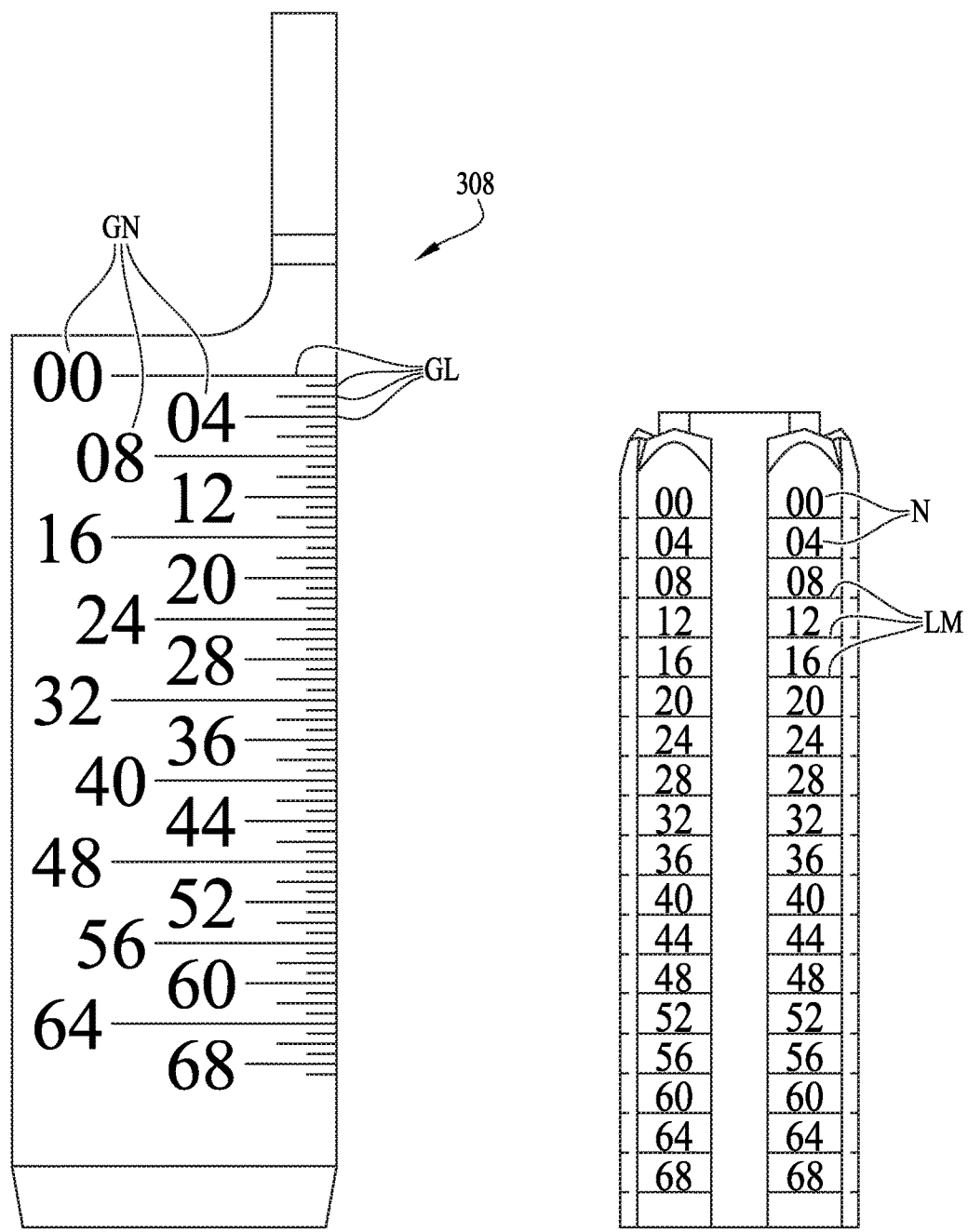
FIG. 20 is a side view of a setting support for the prior art tool setting device of FIG. 19 showing its reference numbers and narrowly spaced apart guide lines.
FIG. 21 is a side view showing a section of the shaft region of the targeter device showing its reference numbers and widely spaced apart guide lines.

It is easy for users to accurately set the degree to which each leg member 160 extends from the elongate landmark guiding structure 110 of the targeter device 100. Some other targeter devices are set by separate tool setting devices. U.S. Pat. No. 10,028,803 teaches one such prior art tool setting device 300, which is shown in FIG. 19. This tool setting device 300 has setting stand 302 with five vertical slots 304 formed on a top 306 therein, and a series of setting supports 308 with depth setting gradient numbers "GN" and gradient lines GL located thereon, in the typical manner of a ruler. FIG. 20 is a front view of one setting support 308 and shows its gradient numbers GN (00, 04, 08, 12, 16, . . . 64, 68) and gradient lines GN. There are gradient lines that separate each adjacent number GN into four units. The setting supports 308 will be positioned in the vertical slots 304 formed in the setting stand 302. To allow for very small adjustments in the heights of the setting supports 308 above the top 306 of the setting stand 302, this means that the gradient markings GN need to be very close together (e.g. 0.5 mm apart). For such closely positioned together gradient lines GN, it can be difficult to discern and accurately set the setting supports 308. In contrast to the difficult to read and distinguish numbers and number lines on the prior art setting supports 308 of FIGS. 19 and 20, as shown in FIG. 21, which shows the one number series 130A section of the shaft region 110 of the targeter device 100, the numbers N with their associated location markers LM on the scaled rulers 120A are set apart in increments of 2 mm, and do not include any other intermediate location marker lines. Thus, the numbers N with their associated location markers LM on the scaled rulers 120A-E are less cluttered and easier to read and align compared to the numbers and gradient lines of the setting supports 308 of the prior art. Moreover, to use this type of prior art tool setting device 300, the user has to first set up the stand and set the positions of its setting supports 310 to desired settings, and then use the tool setting device 300 to adjust the position of the tool (not shown), but similar to the targeter device 100 of the current invention. Such a prior art tool is disclosed in U.S. Pat. No. 9,198,732. This prior art tool does not include any measurement guides to set the longitudinal positions of its leg portions and thus needs to be set using a tool setting device such as disclosed in U.S. Pat. No. 10,028,803.

Turning to FIGS. 13-18, there are shown views of the various elements making up an exemplary locking mechanism 190 of the targeting device 100. The locking mechanism 190 is located near the distal end 106 of the handle 102. In this exemplary embodiment, the locking mechanism 190 comprises several elements. The first is a compression nut 192 having an internally beveled rim 194 that widens from the front 196 towards its rear 198 where internal threads 200 are located. A passage hole 202 is formed through the compression nut 192, through which freely passes the shaft region 116 of the elongate landmark guiding structure 110. At a distal end 106 of the handle 102 there is a clamping area 204. The clamping area 204 includes an externally threaded region 206 with external threads that are complementary to the internal threads 200 of the compression nut 192. Forward of the externally threaded region 206 are a number of locking fingers 208 that consist of elongate fingers 210 that extend forward of the externally threaded region 206 and can be formed as a part thereof and will flex inwardly when pushed on the outside. The elongate fingers 210 are separated by open slots 212. The elongate fingers 210 are present in the same number as there are leg members 160 and complementary grooves 118 and are even spaced around the handle 102 and are aligned with the leg members 160 in the grooves 118. At distal ends 214 of the elongate fingers 210 are distal tips 216 that are preferably inwardly slanted 218 on the outside, on the inside edges 220 of the distal tips 216 there is located at least one protrusion 222 which are designed to catch on spaced apart engagements 254 of the leg members 160. As noted, the through hole 202 passing through the clamping structure 202 is sized to allow the shaft region 116 of the elongate landmark guiding structure 110 to pass therethrough. Thus, as the compression fitting nut 192 is threaded down onto the externally threaded end clamping structure 202, the internally beveled rim 194 will impinge on the separately moveable segments 206 and move them closer together and thereby reduce the spacing of the longitudinal slits 208 and reduce the working diameter of the through hole 210 in the area of the separately moveable segments 206 and the compression fitting nut 192. As this happens, the separately moveable segments 206 will impinge on the slanted outsides of the distal tips 216 and push them inwardly until the at least one protrusion 222 on the inside edges 220 of the distal tips 216 will make contact with and lock together with spaced apart engagements 254 of the leg members 160 and thereby prevent the leg members 160 from being slid in their complementary grooves 118 and thus thereby locking the longitudinal position of each of the leg members 160A-E relative to its applicable groove 118A-E.

In use, the leg members 160 of the adjustable pin setting targeter device 100 are set so that when placed on a surgical site, its longitudinal through hole 124 in the elongate longitudinal landmark guiding structure 110 will have a predetermined position and angular relationship relative to the body tissue. The settings for each of the leg members 160 is established by computer software. This computer software will provide for each of the plurality of elongate leg members a designated unique identifier and provides its associated slide engagements with a designated number N, and having the user directly adjust the longitudinal positions of each of the plurality of elongate leg members relative their associated slide engagements by aligning the sight lines associated with the identified unique identifiers on each leg member with the location marks associated with identified numbers N on each slide engagement. Thus, the user can directly and precisely setup the adjustable pin setting targeter device 100 without having to use a model of the surgical site and without using a pin setting device.

The preferred embodiments of this invention have been disclosed, however, so that one of ordinary skill in the art would recognize that certain modifications would come within the scope of this invention.

What is claimed is:

1. An adjustable pin setting targeter device for body tissue, comprising:
    an elongate longitudinal landmark guiding structure comprising a body with a longitudinal through hole formed therethrough, a plurality of longitudinal slide engagements formed on the body, a unique identifier associated with each longitudinal slide engagements, a plurality of incremented number series equal to a number X wherein the incremented number series are located adjacent to the longitudinal slide engagement, each incremented number series consisting of a plurality of incremented numbers N and associated location marks, wherein in the incremented number series each of the incremented numbers N are incremented from a lowest number to a highest number by the number X, wherein all adjacent location marks associated with incremented numbers N are spaced apart by a distance NS, and wherein the location marks associated with a first number and a last number of each number series are spaced apart by a distance L, and wherein adjacent incremented number series are separated by a distance NSD measured from the location marks associated with the last number and the first number of adjacent incremented number series, and wherein the first number and each subsequent number in each of the incremented number series is increased by one starting from the first incremented number series near the distal end of the elongate longitudinal landmark guiding structure and progressing to each subsequent incremented number series until the X numbered incremented number series is reached; and
    a plurality of elongate leg members, wherein each leg member is slidably engaged with the longitudinal slide engagements of the elongate landmark guiding structure, each elongate leg member comprising X number of longitudinally spaced apart unique identifiers and associated sight lines formed thereon which unique identifiers and associated sight lines are visible when the leg members are slidably engaged with the longitudinal slide engagements, wherein the X number of unique identifiers and associated sight lines are separated by a distance D equal to the distance L+the distance NSD−1/X of the distance NSD;

wherein by sliding each leg member to align with one respective unique identifier and its associated sight line on that leg member with one number in one of the plurality of incremented number series in a respective longitudinal slide engagement, desired longitudinal positions of each leg members can be set.

2. The adjustable pin setting targeter device for body tissue of claim 1, further comprising a locking mechanism to lock in the longitudinal position of the plurality of elongate leg members in the longitudinal slide engagements of the elongate landmark guiding structure.

3. The adjustable pin setting targeter device for body tissue of claim 2, further comprising a handle that is open at least at a distal end to receive the elongate longitudinal landmark guiding structure and wherein the handle includes a locking structure to immobilize a longitudinal and axial positions of the elongate longitudinal landmark guiding structure relative to the handle.

4. The adjustable pin setting targeter device for body tissue of claim 1, wherein the longitudinal slide engagements comprise grooves on an outside of the elongate longitudinal landmark guiding structure, and wherein the elongate leg members comprise elongate strip portions which are slidably received in the grooves.

5. The adjustable pin setting targeter device for body tissue of claim 1, wherein the longitudinal slide engagements comprise pairs of longitudinally arranged and spaced apart scaled rulers positioned on the elongate longitudinal landmark guiding structure, each scaled ruler having the plurality of incremented number series located thereon.

6. The adjustable pin setting targeter device for body tissue of claim 3, wherein the longitudinal slide engagements comprise grooves and the elongate leg members comprise elongate strip portions which are slidably received in the grooves of the elongate longitudinal landmark guiding structure, an extension portion extending away from the elongate strip portion at a distal end thereof, and a terminal foot on the extension portion.

7. The adjustable pin setting targeter device for body tissue of claim 6, wherein each of the plurality of elongate leg member can be identical or can be different in terms of their extension portions and/or terminal feet, and wherein each elongate leg member includes a type identifier.

8. The adjustable pin setting targeter device for body tissue of claim 6, wherein the elongate strip portions of the elongate leg members have an upper surface and near a proximal end of the elongate strip portions there are located spaced apart engagements on the upper surface.

9. The adjustable pin setting targeter device for body tissue of claim 8, wherein the elongate strip portions further comprise a protruding thumb grip protruding from the upper surface thereof.

10. The adjustable pin setting targeter device for body tissue of claim 8, wherein the locking mechanism comprises a plurality of spaced apart locking fingers on the distal end of the handle, a threaded handle portion proximate the locking fingers, wherein the locking fingers each have an inwardly facing catch formed thereon, the locking fingers being aligned with the spaced apart engagements on the upper surfaces of the elongate strip portions of the elongate leg members placed in the grooves of the elongate longitudinal landmark guiding structure, and a compression nut with threads, wherein when the compression nut is threaded onto the threaded portion of the handle, the catches on the locking fingers will be pushed inwardly and impinge on at least one engagement of the elongate leg members and push the leg members inwardly into the grooves and thereby lock the position of the leg members relative to the handle and the elongate longitudinal landmark guiding structure.

11. The adjustable pin setting targeter device for body tissue of claim 1, wherein a desired angular relationship of the longitudinal through hole in the elongate longitudinal landmark guiding structure relative to the body tissue is established by software that provides for each of the plurality of elongate leg members a designated unique identifier and provides its associated slide engagements with a designated number N, and having the user directly adjust the longitudinal positions of each of the plurality of elongate leg members relative their associated slide engagements by aligning the sight lines associated with the identified unique identifiers on each leg member with the location marks associated with identified numbers N on each slide engagements.

12. An adjustable pin setting targeter device for body tissue, comprising:

an elongate longitudinal landmark guiding structure comprising a body with a longitudinal through hole formed therethrough, a plurality of longitudinal grooves formed on the body, a unique identifier associated with each longitudinal groove, a plurality of incremented number series equal to a number X wherein the incremented number series are located adjacent to the grooves, each incremented number series consisting of a plurality of incremented numbers N and associated location marks, wherein in the incremented number series each of the incremented numbers N are incremented from a lowest number to a highest number by the number X, wherein all adjacent location marks associated with incremented numbers N are spaced apart by a distance NS, and wherein the location marks associated with a first number and a last number of each number series are spaced apart by a distance L, and wherein adjacent incremented number series are separated by a distance NSD measured from the location marks associated with the last number and the first number of adjacent incremented number series, and wherein the first number and each subsequent number in each of the incremented number series is increased by one starting from the first incremented number series near the distal end of the elongate longitudinal landmark guiding structure and progressing to each subsequent incremented number series until the X numbered incremented number series is reached, and wherein the elongate longitudinal landmark guiding structure connects to a handle with its distal end extending outwardly therefrom;

a plurality of elongate leg members, wherein each leg member is slidably engaged with the longitudinal grooves of the elongate landmark guiding structure, each elongate leg member having X number of longitudinally spaced apart unique identifiers and associated sight lines formed thereon which unique identifiers and associated sight lines are visible when the leg members are slidably engaged with the longitudinal grooves, wherein the X number of unique identifiers and associated sight lines are separated by a distance D equal to the distance L+the distance NSD−1/X of the distance NSD; and a locking mechanism to lock in the longitudinal position of the plurality of elongate leg members in the grooves of the elongate landmark guiding structure;

wherein by sliding each leg member to align with one respective unique identifier and its associated sight line on that leg member with one number in one of the plurality of incremented number series in a respective longitudinal groove, desired longitudinal positions of each leg members can be set.

13. The adjustable pin setting targeter device for body tissue of claim 12, wherein the handle is open at least at a distal end to receive the elongate longitudinal landmark guiding structure and wherein the handle includes a locking structure to immobilize longitudinal and axial positions of the elongate longitudinal landmark guiding structure relative to the handle.

14. An adjustable pin setting targeter device for body tissue, comprising:

an elongate longitudinal landmark guiding structure having a body with a longitudinal through hole formed therethrough, a plurality of longitudinal grooves formed longitudinally on the body, a unique identifier associated with each longitudinal groove, a plurality of incremented number series equal to a number X wherein the incremented number series are arranged end-to-end in a longitudinal line adjacent to the longitudinal grooves, each incremented number series consisting of a plurality of spaced apart incremented numbers N incremented by the value X and associated location marks, and wherein the elongate longitudinal landmark guiding structure connects to a handle with its distal end extending outwardly therefrom;

a plurality of elongate leg members, wherein each leg member is slidably engaged with the longitudinal grooves of the elongate landmark guiding structure, each elongate leg member having X number of longitudinally spaced apart unique identifiers and associated sight lines formed thereon which unique identifiers and associated sight lines are visible when the leg members are slidably engaged with the longitudinal grooves; and a locking mechanism to lock in the longitudinal position of the plurality of elongate leg members in the longitudinal grooves of the elongate landmark guiding structure;

wherein by sliding each leg member to align one respective unique identifier and its associated sight line on that leg member with one number in one of the plurality of incremented number series in a respective longitudinal groove, desired longitudinal positions of each leg members can be set.

15. The adjustable pin setting targeter device for body tissue of claim 14, wherein in the plurality of incremented number series each of the incremented numbers N are incremented from a lowest number to a highest number by the number X, wherein all adjacent location marks associated with incremented numbers N are spaced apart by a distance NS, and wherein the location marks associated with a first number and a last number of each number series are spaced apart by a distance L, and wherein adjacent incremented number series are separated by a distance NSD measured from the location marks associated with the last number and the first number of adjacent incremented number series, and wherein the first number and each subsequent number in each of the incremented number series is increased by one starting from the first incremented number series near the distal end of the elongate longitudinal landmark guiding structure and progressing to each subsequent incremented number series until the X numbered incremented number series is reached, and wherein the X number of unique identifiers and associated sight lines are separated by a distance D equal to the distance L+the distance NSD−1/X of the distance NSD.

16. The adjustable pin setting targeter device for body tissue of claim 14, wherein the handle is open at least at a distal end to receive the elongate longitudinal landmark guiding structure and wherein the handle includes a locking structure to immobilize longitudinal and axial positions of the elongate longitudinal landmark guiding structure relative to the handle.

17. The adjustable pin setting targeter device for body tissue of claim 14, wherein the elongate leg members comprise elongate strip portions which are slidably received in the grooves of the elongate longitudinal landmark guiding structure, an extension portion extending away from the elongate strip portion at a distal end thereof, and a terminal foot on the extension portion.

18. The adjustable pin setting targeter device for body tissue of claim 17, wherein the elongate strip portions of the elongate leg members have an upper surface and near a proximal end of the elongate strip portions there are located spaced apart engagements on the upper surface and wherein the locking mechanism comprises a plurality of spaced apart locking fingers on a distal end of the handle, a threaded portion proximate the locking fingers, wherein the locking fingers each have an inwardly facing catch formed thereon, the locking fingers being aligned with the spaced apart engagements on the upper surfaces of the elongate strip portions of the elongate leg members placed in the grooves of the elongate longitudinal landmark guiding structure, and a compression nut with threads, wherein when the compression nut is threaded onto a threaded portion of the handle, the catches on the locking fingers will be pushed inwardly and impinge on at least one engagement of the elongate leg members and push the leg members inwardly into the grooves and thereby lock the position of the leg members relative to the handle and the elongate longitudinal landmark guiding structure.

19. The adjustable pin setting targeter device for body tissue of claim 14, wherein a desired angular relationship of the longitudinal through hole in the elongate longitudinal landmark guiding structure relative to the body tissue is established by software that provides for each of the plurality of elongate leg members a designated unique identifier and provides its associated slide engagements with a designated number N, and having the user directly adjust the longitudinal positions of each of the plurality of elongate leg members relative their associated slide engagements by aligning the sight lines associated with the identified unique identifiers on each leg member with the location marks associated with identified numbers N on each slide engagements.

* * * * *